United States Patent [19]

Capone

[11] 4,115,229

[45] Sep. 19, 1978

[54] APPARATUS FOR SAMPLING A GASEOUS STREAM

[75] Inventor: David M. Capone, Oakmont, Pa.

[73] Assignee: Thermo-Lab Instruments, Inc., Pittsburgh, Pa.

[21] Appl. No.: 739,724

[22] Filed: Nov. 8, 1976

[51] Int. Cl.² .................................................. G01N 27/46
[52] U.S. Cl. ..................................... 204/195 S; 73/23; 73/421.5 R; 204/1 T; 23/232 E; 422/83; 422/98
[58] Field of Search ................. 73/23, 27 R, 421.5 R; 204/1 S, 195 S; 23/232 E, 254 E, 255 E

[56] References Cited

U.S. PATENT DOCUMENTS

| Re. 29,209 | 5/1977 | Sayles | 73/23 |
|---|---|---|---|
| 1,504,707 | 8/1924 | Peters | 73/27 R |
| 1,874,549 | 8/1932 | Krueger et al. | 73/27 R |
| 2,807,159 | 9/1959 | Wilson | 73/27 R |
| 3,791,936 | 2/1974 | Pebler et al. | 204/195 S |
| 3,960,500 | 6/1976 | Ross et al. | 73/421.5 |

*Primary Examiner*—T. Tung
*Attorney, Agent, or Firm*—Stanley J. Price, Jr.; John M. Adams

[57] ABSTRACT

A gas analyzer is provided with a common inlet-outlet chamber through which all gases must travel to enter or exit the flow circuit.

5 Claims, 3 Drawing Figures

APPARATUS FOR SAMPLING A GASEOUS STREAM

BACKGROUND OF THE INVENTION

1. Field of the Invention

This invention relates to a method and apparatus for sensing the condition of a gas, and more specifically, to a method and apparatus particularly suitable for analyzing dirty gas and/or gas containing an explosive mixture. As used in this specification, the term "condition" or "condition of a gas" is intended to refer to either the physical or chemical or other properties of the gas being analyzed.

2. Description of the Prior Art

Gas analyzers that utilize a convection loop or bring a portion of the sample up past a gas sensing element and back into the main sample flow stream are used for the analysis of gaseous combustion products from combustion processes, particularly those involving suspended solids in the gas products. However, such analyzers suffer from two distinct disadvantages:

a. When the sample contains a high concentration of low-density solids, these may be carried upwards into the heated section of the flow loop where they become concentrated because of reduced velocity due to changes in the flow path diameter and/or the lower density and viscosity of the gas at the location and, thus, cause plugging of the systems; and b. if the sample contains an explosive mixture of gas consisting of sufficient oxygen and fuel gas to ignite, this sample will be ignited in the heated sections of the flow path and the resulting explosion can propagate through the sample flow path to the chamber from which it originated.

Accordingly, there is a need for a method and apparatus particularly adapted for analyzing dirty gas and/or gas containing an explosive mixture without encountering the risk of plugging the analyzer system or precipitating an unwanted explosion.

SUMMARY OF THE INVENTION

In accordance with the present invention, there is provided a method and apparatus for efficiently and safely analyzing the condition of dirty gas and/or gas containing an explosive mixture on a continuous basis. In particular, this invention provides a method and apparatus for analyzing gas utilizing a convection loop flow circuit to bring a gas sample up past a gas sensing element, such as a heated ceramic electrochemical cell, a catalytic combustibles detector or other gas detector, and back to a common inlet-outlet chamber at the main flow path where all or part of the convection loop flow intercepts and is discharged back into the same passageway through which the sample gas flows upwards toward the sensing element. By operating in this manner, the net upward flow velocity is zero or substantially zero so that only a negligible amount of solids will be lifted above this common inlet-outlet chamber up into the portion of the convection loop where the flow is upward.

Moreover, when the principles of this invention are employed to analyze explosive mixtures of combustible gases and oxygen, the stream reaching the section in which the gas sample is heated to be analyzed is a mixture of fresh sample and already-burned sample. More specifically, for example, a portion of the gas that has passed by a heated electrochemical cell or catalytic combustibles detector and therefore has been brought to chemical equilibrium by burning is mixed with fresh sample and recirculated back to the heated cell so that, in the event an explosive mixture enters the apparatus, the mixture will be diluted with sufficient already burned sample such that an explosion cannot occur, nor propagate in either direction from the convection loop.

The foregoing and other objects, features and advantages of this invention will become more apparent when taken in conjunction with the following specification, the accompanying drawings and the appended claims.

DESCRIPTION OF THE PREFERRED EMBODIMENTS

Figure 1:
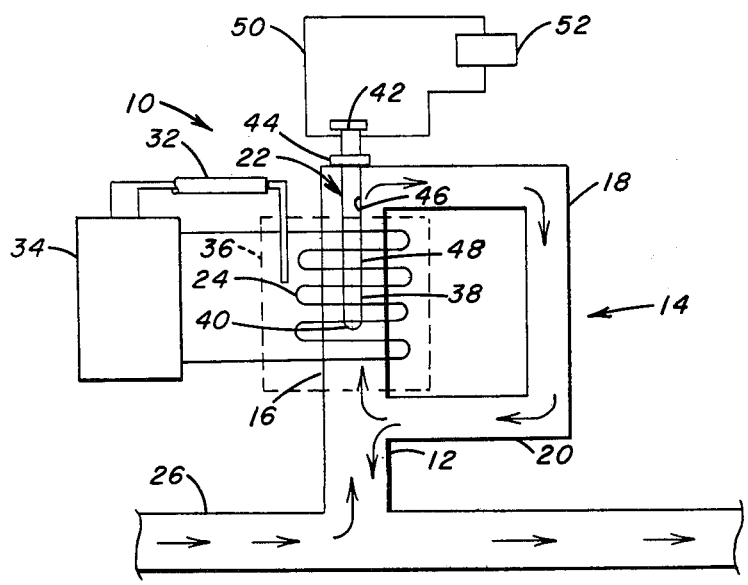
FIG. 1 is a schematic representation of a novel analyzer flow circuit of this invention.

Referring to FIG. 1, there is shown a preferred convection gas analyzer 10 of this invention. Gas analyzer 10, as shown, is comprised of a common inlet-outlet chamber of junction conduit 12, a loop conduit 14 having an inlet portion 16, an intermediate loop portion 18 and an outlet portion 20, a gas condition sensing device 22 and a heater 24 to induce a continuous flow of sample gas by convection, in the direction of the arrows shown, through the analyzer. As will be apparent, inlet portion 16 and outlet portion 20 of loop conduit 14 are connected in fluid flow communication with junction conduit 12 which, in turn, is connected in fluid flow communication with main passageway 26.

To provide a predictable continuous flow of gas through gas analyzer 10, a temperature differential is maintained between the inlet portion or leg 16 and the outlet portion or leg 20 of loop conduit 14 by heater element 24 positioned around inlet portion 16. The heater element 24 is controlled by means of a temperature sensor 32 such that the temperature in the inlet portion 16 is maintained at a preselected value, preferably in the range of 600° F to 1800° F for an electrochemical cell and below the ignition temperature of entrained combustibles for a catalytic combustibles detector, by means of a conventional temperature controller 34. An enclosure 36 houses the heater element 24 to confine the increased temperature to the inlet portion or leg 16 to maintain the desired temperature differential between the inlet portion 16 and the outlet portion 20 of loop conduit 14. It will be apparent that with this arrangement the temperature of the inlet portion 16 of the loop conduit 14 will be maintained at a higher temperature than the outlet portion 20. Although a heater element is illustrated for maintaining this temperature differential, it will also be apparent that this temperature differential could be enhanced, or even independently maintained, by cooling the outlet portion 20 and thereby providing a temperature differential between the inlet portion 16 and the outlet portion 20 to obtain convective flow. Moreover, when employing a catalytic combustibles detector, it will be understood by those skilled in the art that operation of the catalytic detector above may provide sufficient convective flow and, under such circumstances, heater element 24 may be dispensed with.

The sensing device 22 illustrated in FIG. 1 of the drawings is a ceramic oxide electrochemical cell that measures the oxygen partial pressure of the sample. This sensing device includes a tube 38 of ceramic oxide material having a closed end portion 40 and an open end portion 42. The tube is positioned in inlet portion 16 with the closed end portion facing into or toward the gas flow path and the open end of the tube extending beyond the seal 44. The inside of tube 38 is provided with a porous conductive electrode coating 46 and the outside of the tube is provided with a similar porous conductive electrode coating 48. The coatings or electrodes 46 and 48 are connected through a circuit 50 to a voltage measuring device 52 which is arranged to indicate the EMF produced by the electrochemical cell. Electrochemical cells for measuring oxygen partial pressure are well known and suitable cells for use with this invention are disclosed in U.S. Pat. Nos. 3,597,345 and 3,869,370, the disclosures of which are incorporated herein by reference.

In accordance with the practice of this invention, heater 24 will induce, by convection, a continuous flow of sample gas from main passageway 26, through junction conduit 12 and past sensing device 22 in inlet portion 16 of loop conduit 14, with the sample then passing through intermediate loop portion 18 and outlet portion 20 of the loop conduit. As the sample gas exits outlet portion 20 into inlet-outlet or junction chamber 12, it intermingles by a combination of diffusion and turbulence with the intercepted incoming or fresh gas sample such that, as explained hereinabove, the flow velocity of the incoming gas sample is reduced to zero or substantially zero or controlled to a rate that is inadequate to suspend a significant amount of solids and/or is diluted with sufficient combustion products such that an explosion cannot occur, nor propagate in either direction from the convection loop 14.

Figure 2:
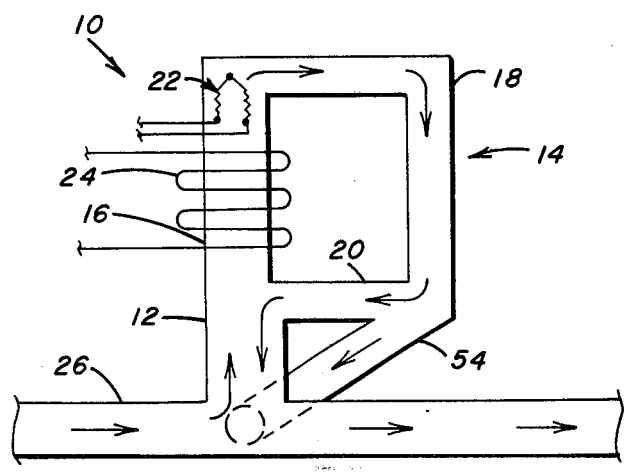
FIGS. 2 and 3 are additional schematic representations of novel analyzer flow circuits according to the principles of this invention.
Figure 3:
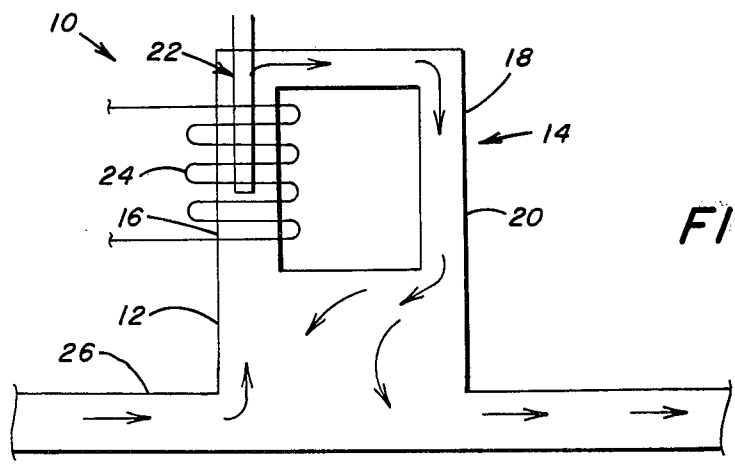

Shown in FIGS. 2 and 3 are alternative embodiments of this invention in which like numerals have been employed to designate like parts throughout the same. No extensive description of these alternative embodiments is deemed necessary, since the function and operation thereof remain essentially the same as described in connection with FIG. 1, the principal difference inhering in use of other gas sensing elements and in variations in constructional features and relative dimensions for purposes suited to particular applications. For example, in FIG. 2 there is shown schematically a catalytic combustibles detector, such as disclosed in U.S. Pat. Nos. 1,504,707 or 3,522,010, being employed for sensor device 22. Also shown is an additional conduit 54 interconnecting outlet portion 20 of loop conduit 14 to main passageway 26 where it interconnects with junction conduit 12, thereby providing a flow path returning sample to junction conduit 12, and a flow path returning sample to main passageway 26, the purpose of which is to provide partial recirculation of combustion products such that the flow of incoming gas is diluted sufficiently with burned sample to prevent an explosion or propagation of flame in either direction from the convection loop. Moreover, in FIG. 3 is shown a sensor device 22 of any desired type and, in addition, an enlarged junction conduit 12 from that shown in FIG. 1 whereby, as with the FIG. 2 variant, the particularly desired level of turbulence and diffusion may be modified, compared to the FIG. 1 construction, to suit a particular application.

According to the provisions of the patent statutes, I have explained the principle, preferred construction and mode of operation of my invention and have illustrated and described what I now consider to represent its best embodiments. However, it should be understood that, within the scope of the appended claims, the invention may be practiced otherwise than as specifically illustrated and described.

I claim:

1. Apparatus for sampling a gaseous stream flowing in a main passageway comprising, a main passageway with a gaseous stream flowing therethrough, a closed loop conduit having an inlet portion, an intermediate portion and an outlet portion, a junction conduit in fluid communication with said main passageway and said closed loop conduit arranged to convey a sample of said gaseous stream from said main passageway to said closed loop conduit inlet portion and a portion of the analyzed sample from said closed loop conduit outlet portion to said main passageway, said junction conduit positioned in fluid flow communication with said inlet and outlet portions of said loop conduit and providing a common ingress for said sample to said closed loop conduit and egress for a portion of said analyzed sample from said closed loop conduit causing the recirculation of a portion of said analyzed sample in said closed loop conduit, convection means operatively associated with said loop conduit to maintain a temperature differential between said inlet portion and said outlet portion to induce a convective continuous flow of sample gas through said junction conduit and said closed loop conduit, and sensing means in the flow path through said loop conduit for sensing the condition of sample gas.

2. Apparatus according to claim 1 wherein said means to induce continuous flow comprises a heater operatively associated with said inlet portion of said closed loop conduit.

3. Apparatus according to claim 2 wherein said sensing means comprises a ceramic oxide electrochemical cell.

4. Apparatus according to claim 3 wherein said electrochemical cell is disposed adjacent said heater.

5. Apparatus according to claim 1 wherein said sensing means comprises a catalytic combustibles detector.

* * * * *